(12) United States Patent
Eisenhauer et al.

(10) Patent No.: US 9,470,665 B2
(45) Date of Patent: Oct. 18, 2016

(54) METHOD FOR VERIFYING AGE-DEPTH RELATIONSHIPS OF ROCK IN SEDIMENTARY BASINS

(75) Inventors: Anton Eisenhauer, Heikendorf (DE); Dietrich Horn, Essen (DE)

(73) Assignee: GEOMAR Helmholtz-Zentrum fuer Ozeanforschung Kiel, Kiel (DE)

(*) Notice: Subject to any disclaimer, the term of this patent is extended or adjusted under 35 U.S.C. 154(b) by 121 days.

(21) Appl. No.: 14/342,828

(22) PCT Filed: Aug. 30, 2012

(86) PCT No.: PCT/DE2012/100256
§ 371 (c)(1),
(2), (4) Date: Mar. 5, 2014

(87) PCT Pub. No.: WO2013/034143
PCT Pub. Date: Mar. 14, 2013

(65) Prior Publication Data
US 2014/0224001 A1  Aug. 14, 2014

(30) Foreign Application Priority Data
Sep. 5, 2011 (DE) .................. 10 2011 112 292

(51) Int. Cl.
*G01N 30/06* (2006.01)
*G01V 5/06* (2006.01)
*G04F 13/00* (2006.01)
*G01N 30/02* (2006.01)

(52) U.S. Cl.
CPC .............. *G01N 30/06* (2013.01); *G01V 5/06* (2013.01); *G01N 2030/027* (2013.01); *G04F 13/00* (2013.01)

(58) Field of Classification Search
USPC ............. 73/112.03; 436/25; 405/236
See application file for complete search history.

(56) References Cited

U.S. PATENT DOCUMENTS

2006/0116823 A1  6/2006  Griffiths

FOREIGN PATENT DOCUMENTS

EP  1435429 A1  7/2004
WO  WO 2011077271 A1 *  6/2011 ........... E21B 49/082

OTHER PUBLICATIONS

Teichert B M A et al: "Controls on calciumisotope fractionation in sedimentary porewaters", Earth and Planetary Science Letters, North Holland Publ, Co, NL,vol. 279, No. 3-4, Mar. 30, 2009, pp. 373-382, XP026000615, ISSN: 0012-821x, DOI:10.1016/J.epsl.2009.01.011.*
International Search Report dated Jul. 15, 2013, in International Application No. PCT/DE2012/100256.
Gussone N et al: "Reconstruction of Caribbean Sea surface temperature and salinity fluctuations in response to the Pliocene closure of the Central American Gateway and radiative forcing, using delta<44/40>CA, delta<18>O and Mg/Ca ratios", Earth and Planetary Science Letters, North Holland Publ., Co, NL, vol. 227, No. 3-4, Nov. 15, 2004, pp. 201-214, XP004613614, ISSN: 0012-821X, DOI: 10.1016/J.EPSL.2004.09.004, the whole document.
Teichert B M A et al: "Controls on calcium isotope fractionation in sedimentary porewaters", Earth and Planetary Science Letters, North Holland Publ., Co, NL, vol. 279, No. 3-4, Mar. 30, 2009, pp. 373-382, XP026000615, ISSN: 0012-821X, DOI: 10.1016/J.EPSL.2009.01.011 [retrieved on Feb. 15, 2009] the whole document.

* cited by examiner

*Primary Examiner* — Michael A Lyons
*Assistant Examiner* — Jean Morello
(74) *Attorney, Agent, or Firm* — Patent Central LLC; Stephan A. Pendorf

(57) ABSTRACT

Method for verification of age-depth relationships of rocks in sedimentary basins by reconstructing the subsistence rate of samples, in which, by determining the precipitation depth and precipitation temperature of a carbonate precipitation, wherein by determining the precipitation depth and the precipitation temperature of the carbonate precipitation in the geological-history-determining sedimentary rocks, from which a sample is taken, a set point is fixed.

7 Claims, 4 Drawing Sheets

METHOD FOR VERIFYING AGE-DEPTH RELATIONSHIPS OF ROCK IN SEDIMENTARY BASINS

The invention relates to a method for the verification of age-depth relationships of rocks in sedimentary basins according to the preamble of the main claim. This verification can be used in general in the field of oil and gas exploration. In particular, the invention provides a method for validation and calibration of mathematical models of sedimentary basins (sedimentary basins such as the North German Basin).

Sedimentary basins are those regions in which the earth's crust subsides due to sediment deposition. Sediment eroded from the continents is transported by rivers or ocean currents and is deposited in them. New sediment layers are continuously deposited one on the other, causing the basin to fill and the earth crust to be pressed into the mantle.

In sedimentary basins, large amounts of organic matter are stored, which can be converted to natural gas and oil in geological time periods due to the effect of temperature and pressure. A crucial parameter for the exploration of natural gas or petroleum is the knowledge of the depth of the oil-bearing strata. By way of example, most of the oil being pumped today came from the Jurassic age. This layer is now, of course, no longer at the surface but has been moved to a certain depth below the earth surface (about 1 to 2 km) by the overlaying of layers of younger deposits. The oil deposit to be pumped, since it is lighter than water, collects higher up in the Jurassic layer. It is therefore important to know where the "Jurassic" is below the surface, and the general trend of the vertical downward movement, but in certain cases also the upward movement, over time. This can be described in an age-depth relationship, which can be represented in a diagram in which the depth of the rock layer below the earth's surface is shown as a function of time. This age-depth relationship is determined using mathematical modeling, so-called basin models.

A basin model is a discrete mathematical representation of a geologic basin in the form of a plurality of cells that form a mesh network (finite elements). The simulator model of a basin makes it possible to calculate in each cell a certain number of parameters. The aim of basin modeling is to produce an age-depth relationship for the sedimentary basin, from which then the location of certain oil- and gas-carrying layers, can be predicted as a function of time or period. Based on this prediction decisions are made, as to whether the so-called sinking of exploratory drillings is successful or not. The cost of drilling are high, so that accurate predictions of the basin models are an important imputed items in oil or gas-exploration.

The publication EP 1435429 A1 discloses a method and a system for time-delayed analysis of cause and effect of changes in a wellbore interval, wherein a first log data is detected with a logging sensor during a first pass through the wellbore interval and a second log data is acquired by the logging sensor during a second pass over the wellbore interval at a time later than the first log data, a plurality of delta values are calculated between the first log data and the second log data, an observed effect is derived using the delta values and subsequently a correlation between the observed effects and a causal event is identified, and the correlation is displayed on a display device.

The difficulty in basin modeling is that there may be considerable individual differences from basin to basin due to tectonic movements and other geological processes. The individual mathematical modeling of a sedimentary basin, also for determining the relative vertical movement of a layer, in a basin taking into account all factors of various magnitudes influencing subsidence has not yet been solved satisfactorily.

To increase the accuracy and veracity of basin models, it would therefore be advantageous if "fixed points" were known for a basin and its basin model, which enable establishment of an age-depth relationship, regardless of the basin model, and thus to validate and calibrate the basin models with an independently created age-depth relationship.

It is the object of the invention to provide a method which makes possible a verification of the age-depth relationships determined by any means, for validation and possibly calibration of sedimentary basin models by determining an age-depth relationship.

The inventors have discovered that the object of the invention can be solved when a method is used to determine the age-depth relationship, which is comprised of e.g. the following steps:

i. dissolution of the precipitated calcium carbonate from sedimentary rocks by use of dilute acids (→ Solution A), ii. determination of the Ca isotope ratio of the two most common isotopes $^{40}Ca$ and $^{44}Ca$ ($^{44}Ca/^{40}Ca$) or even another Ca—isotope ratio for the determination of the isotope ratio of the precipitated $CaCO_3$ (CC). The ratio may be indicated in the delta notation customary in isotope geology ($\delta^{44/40}Ca_{CC}$).

iii. calculating the Ca isotopic difference ($\Delta^{44/40}Ca$) between the solution (BS=Bulk Solution) and the $CaCO_3$ (CC) precipitated from the solution according to ($\Delta^{44/40}Ca = \delta^{44/40}Ca_{CC} - \delta^{44/40}Ca_{BS}$) if $\delta^{44/40}Ca_{BS}$ is known. Otherwise, first determine the $\delta^{44/40}Ca_{BS}$-value.

iv. determining the $CaCO_3$ precipitation temperature across the relationship $\Delta^{44/40}Ca$ (‰)=0.02 (‰/° C.)*temperature (° C.)−1.46‰ (Gussone et al. 2004) according to Equation 1.

$$T(°C.) = \frac{\Delta^{44/40}Ca + 1.46}{0.02} \qquad \text{Equation 1}$$

V. determining the $CaCO_3$ precipitation depth (X in meters (m)) is determined using Equation 2.

$$X(m) = \frac{\delta^{44/40}Ca_{CC} - \delta^{44/40}Ca_{BS} + 1.16}{0.00066} \qquad \text{Equation 2}$$

If $\delta^{44/40}Ca_{BS}$ is not known, then the following steps are necessary:

a) separation and recovery of strontium ions ($Sr^2$) from solution A, for example, by on chromatography.

b) determination of Sr isotope ratio $^{87}Sr/^{86}Sr$ or another strontium isotope ratio of the separated strontium ion ($Sr^{2+}$).

c) determining the age of the sample by comparing the measured $^{87}Sr/^{86}Sr$-isotope relationship with the known Sr isotope ratio of Phanerozoic sea water (FIG. 2).

d) determining the $\delta^{44/40}Ca_{BS}$ based on known correlations (FIG. 3).

Then proceed with step iv.

It may be beneficial if prior to the determination of the Ca isotope ratio (step ii) a solution of known isotopic composition Ca (spike solution) is added for calibration.

The dissolution of the precipitated calcium carbonate from sedimentary rocks by means of dilute acids (step i) should be done with a weak organic or inorganic acid, e.g. formic acid or 2N $HNO_3$ to ensure that no calcium is leached from the non-calcium carbonate host rock, i.e., it is made sure that the original calcium isotopic composition of the calcium carbonate precipitated from the rock can be measured. The skilled worker is familiar with suitable acids and their strengths.

The inventors were first to recognize that the phenomenon of temperature-dependent calcium isotope fractionation during the precipitation of calcium carbonate ($CaCO_3$) in porous rocks can be exploited to determine an empirical age-depth relationship.

From the context of precipitation temperature ($T_{precipitation}$), depth and geogenic temperature increase as a function of depth an empirical age-depth relationship can be determined for several depths (fixed points). These values can then be compared with the basin model calculated theoretical values. These fixed points enable calibration of basin models which can lead to an improvement in the identification of oil-bearing strata and savings in drilling costs.

With the maturation of the oil, large amount of methane ($CH_4$) and possibly carbon dioxide ($CO_2$) are produced, which rises in the rock strata and reacts with the sea water still existing in the rock (mostly from the Jurassic sea, but also waters from other epochs) and converts the therein dissolved calcium to calcium carbonate ($CaCO_3$). This takes place in a certain depth above the oil-bearing strata, which is uniquely characterized by pressure and in particular temperature. In particular, the $T_{precipitation}$ is defined by the geogenic gradient with a temperature increase of ~0.033° C./m (the rule of thumb here is an increase of 3° C. per 100 m depth in the earth). In other words, at about 100 m depth, the temperature is about 3.3° C. higher than at the surface. The actual temperature at 100 m depth is then obtained from the average temperature at the surface of ~15° C. and the geogenic increase ($T_{precipitation}$) of 3.3° C., i.e., one can presume a temperature in the order of ~18.3° C. ($T_{geogenic}$=15° C. (0.033° C./m)*Depth (m)) at a depth in the earth of 100 m. The geogenic, increase of temperature with depth is a rule of thumb that can vary within a certain statistical framework. The actual temperature profile in a sedimentary basin can be corrected by the direct temperature measurements in a wellbore.

Regardless of the geogenic connection $T_{precipitation}$ can be reconstructed by the measurement of a specific Ca-isotope ratio (here: $^{44}Ca/^{40}Ca$). When comparing $T_{precipitation}$ with $T_{geogenic}$ it is found that as a rule $T_{precipitation}$ is always less than $T_{geogenic}$ ($T_{precipitation} < T_{geogenic}$). This is because the increased drilled depth where the rocks are drilled today and of course a higher temperature than the corresponding depth at which the calcium carbonate precipitation took place, usually many millions of years earlier.

The Ca isotopy of calcium carbonate ($CaCO_3$, calcite and aragonite) is temperature dependent, in the manner, that for kinetic reasons the negative Ca isotopic difference between the solution (BS=Bulk Solution) and the $CaCO_3$ (CC) precipitated from the solution as function of temperature (see equation) keeps getting smaller.

$$\Delta^{44/40}Ca = \delta^{44/40}Ca_{CC} - \delta^{44/40}Ca_{BS}$$

According to the following equation $\Delta^{44/40}Ca$ (=fractionation factor) is relatively large for low and small for higher temperatures. The isotopic equilibrium (equivalent value of CC and BS) is reached in accordance therewith at a temperature of approximately 73° C., at which there is no more isotopic difference between BS and CC. A temperature reconstruction is therefore only possible in the temperature interval to ≤73° C.

$$T(°C.)=\Delta^{44/40}Ca+1.46)/10.02$$

The equation is true for temperatures <73° C.~($\Delta^{44/40}Ca$=0). $\Delta^{44/40}Ca$ is expressed in per mil (‰).

Assuming the general geothermal gradient of 0.033° C./m and an average temperature at the surface of approximately 15° C., then the temperature-dependence of the Ca isotope can be converted into a depth-dependence, according to the following equation. This means that if there is a $CaCO_3$ precipitation in the geological depth, the $\Delta^{44/40}Ca$ isotope value clearly reflects the geological depth and temperature, making it thus possible to reconstruct the geological subsidence rate and history.

$$\Delta^{44/40}Ca(m)=\lfloor15+0.033\cdot X(m)\rfloor\cdot0.02-1.46$$

For temperature determination with $CaCO_3$ precipitation here is needed, besides the Ca isotopic composition of the precipitated $CaCO_3$ precipitation ($\delta^{44/40}Ca_{CC}$), also an indication of the Ca isotopic composition of the parent solution ($\delta^{44/40}Ca_{BS}$) is required. The relationship between precipitated $CaCO_3$ (CC) ($\delta^{44/40}Ca_{CC}$), the parent solution BS ($\delta^{44/40}Ca_{BS}$), the geothermic gradient and the depth X(m) in the earth's crust during $CaCO_3$ precipitation can be determined by $$\delta^{44/40}Ca_{CC}=[15+0.033\cdot X(m)]\cdot0.02-1.46+\delta^{44/40}Ca_{BS}$$

To Equation 2

$$X(m) = \frac{\delta^{44/40}Ca_{CC} - \delta^{44/40}Ca_{BS} + 1.16}{0.00066} \quad \text{Equation 2}$$

FIG. 1 shows graphically the relationship between the Ca-isotope fractionation, the temperature (T) and the depth (X).

For the determination of $\delta^{44/40}Ca_{BS}$ the calcium isotopic composition of the parent solution (BS) must be known, such as by sea water of the corresponding geological depositional environment. If no original solutions are any longer present, the age of the parent solution, from which the carbonates have precipitated, can be determined by a determination of the $^{87}Sr/^{86}Sr$ isotope ratios of the strontium ions ($Sr^{++}$) extracted from the sedimentary rock and the comparison with the Phanerozoic $^{87}Sr/^{86}Sr$-seawater curve. Such a $^{87}Sr/^{86}Sr$-seawater curve is shown in FIG. 2.

If the age of he parent solution is known, then the $\delta^{44/40}Ca_{BS}$ a can be read from FIG. 3.

The ($CaCO_3$) precipitation temperature and depth of the precipitated $CaCO_3$ is then obtained according to Eq. 2.

The determination of Ca and Sr isotope ratio can take place with the help of mass spectrometry (MS). In the following, this method will be explained in more detail by way of example, with the aid of which the method of the invention can be performed, the person of ordinary skill will, in certain cases, make changes to individual process parameters in the manner known to him.

The eluate, which contains substantially only the calcium, is concentrated to about 1 μl and applied to an approximately 1 mm wide and rhenium wire, the so-called filament. This sample is then mounted in the thermal ionization unit of a mass-spectrometer. After the ionization unit is evacuated and the pressure therein is lower than 10-6 mbar, the filament is gradually heated until it becomes red hot. Thereby the calcium on the filament and its isotopes $^{40}$Ca and $^{44}$Ca is thermally evaporated and ionized. The evaporated ions enter into an applied electric field with an accelerating voltage of about 10,000 volts. The accelerated ions, which must pass different ion-optical lenses, reaching magnets which provide, on the basis of the mass-dependent equilibrium of the Lorentz force and the centripetal force, for a splitting of the ion beam. The lighter ions (here $^{40}$Ca) fly a tighter radius than the heavier ions (here $^{44}$Ca). After passing the magnet, the ions hit detection units, the so-called Faraday beaker, where the ions are slowed down by a conductive or guiding layer. The ions generate an electrical current in this beaker, which flows through a high-impedance resistor (~$10^{11}$ ohms) and generates a relatively high electrical voltage, which can be easily measured. This is done individually for each ion, so that for evaluating intensity one can evaluate the measured voltage. The number of ions flowed then is obtained from the ratio of the masses, since the voltage is directly proportional to the flowed ions per time. The evaluation is computer-assisted via a known algorithm.

After measuring the $\delta^{44/40}$Ca and $^{87}$Sr/$^{86}$Sr-values the following parameters of the sample are now known:
1. The temperature during the time of precipitation ($T_{precipitation}$) of CaCO$_3$ determined from the equation 1, values and $\delta^{44/40}$Ca.
2. The depth ("CaCO$_3$ precipitation depth") below the surface in which the precipitation took place, determined from the $\delta^{44/40}$Ca-values and the equation 2.
3. From the borehole depth and the known age of the rock layer, the subsidence rate can be determined [(drilling depth (m))/(age of the rock ( ) Ma)=subsidence rate (m/Ma)].

As a result of the procedure one obtains an age depth relationship for a rock, just as one would also pursue using mathematical basin modeling. These relationships can now be shown in an empirical age-depth relationship (empirical model of the basin) (FIG. 5). The proposed values according to our process now allow a validation of the values of the basin model based on theoretical assumptions and on seismic profiles. Ideally, the values determined from our method match the values from the basin modeling. In this case, the basin model is reliable.

In the case of discrepancy, when empirical and theoretical values do not match, the assumptions on which the basin model is based must be reviewed and, if necessary, changed, so that both approaches can be brought into agreement ("calibration of the basin model"). From this there may result in a change of the prediction for the location of the oil-bearing layers and a corresponding adjustment to the desired drilling depth.

The subsidence of the rocks after they have left the earth's surface is not usually linear and can only be reconstructed on complex mathematical basin models within certain ranges. The comparison of the theoretically determined age—depth relationship of a particular basin with the age—depth relationship values determined by our method then gives important clues to the linearity of the reduction. For larger deviations, it must then be assumed that there was a non-linearity of the subsidence or wrong model approaches. In any case in the latter case the revision of the underlying mathematical model is required.

The comparison of the introduced mathematical model of the basin with empirical age—depth relationships and/or to calibrate increases the reliability of basin models, increases the hit probability of oil-bearing layers and saves drilling costs.

Further advantages and features of the invention will become apparent from the following description of a preferred embodiment with reference to the accompanying drawings, In the drawings.

Figure 4:
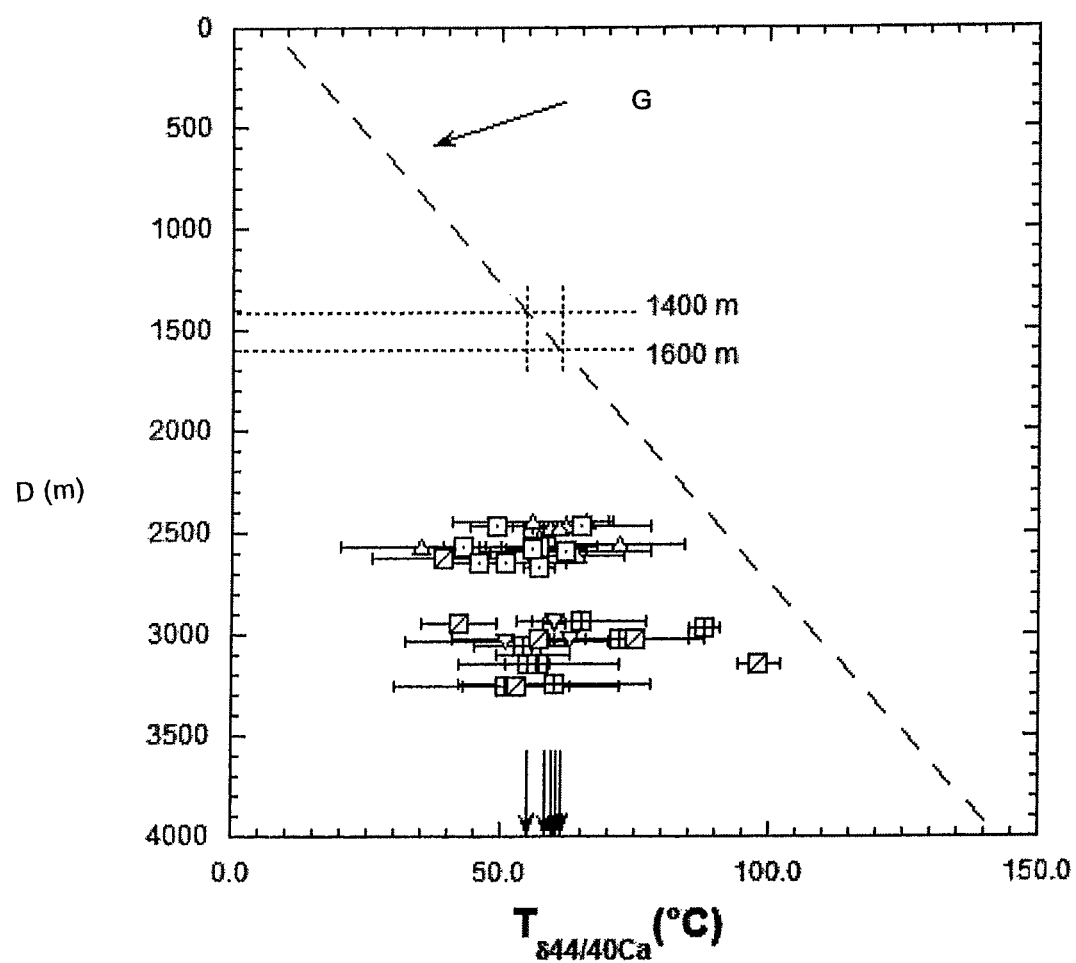

FIG. 4 shows the temperature values (° C.) determined according to the invention from Table 1 as a function of their depth. The symbols correspond to very specific drill sites. The arrows in the representation mark respectively the average precipitation temperatures for the various symbols or locations. Together with the data points of different locations, the thermal gradient is illustrated.

Figure 5:
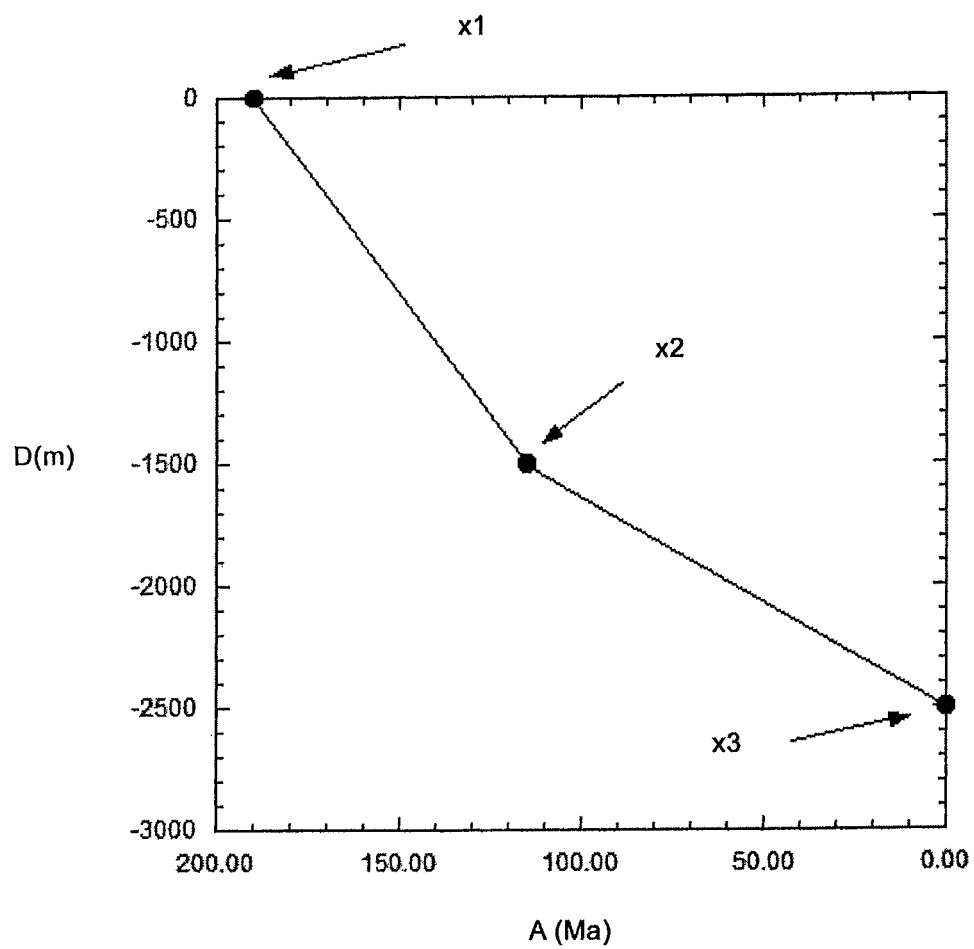

FIG. 5 shows an example of an inventive determined empirical age-depth relationship (empirically developed model of the basin) from the measured values. From the empirically determined fixed point, the non-linearity of the subsidence rate can be clearly seen.

Figure 1:
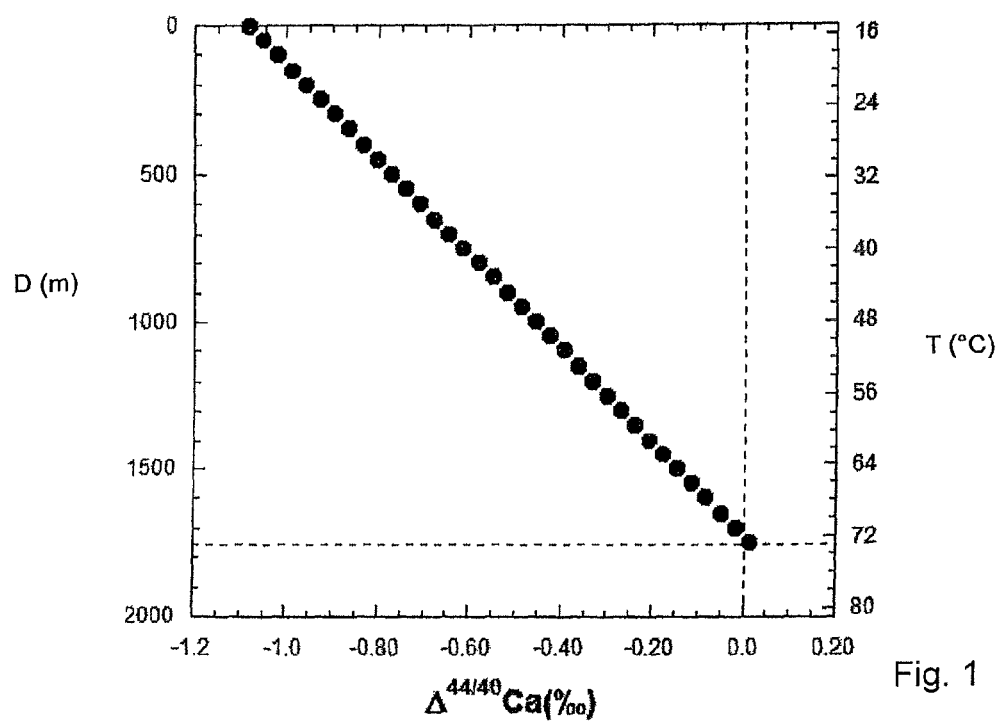
FIG. 1 shows the dependence of $\Delta^{44/40}$Ca$_{CC}$ values as a function of depth (left axis) and temperature (right axis) of the Ca isotope ratio.
Figure 2:
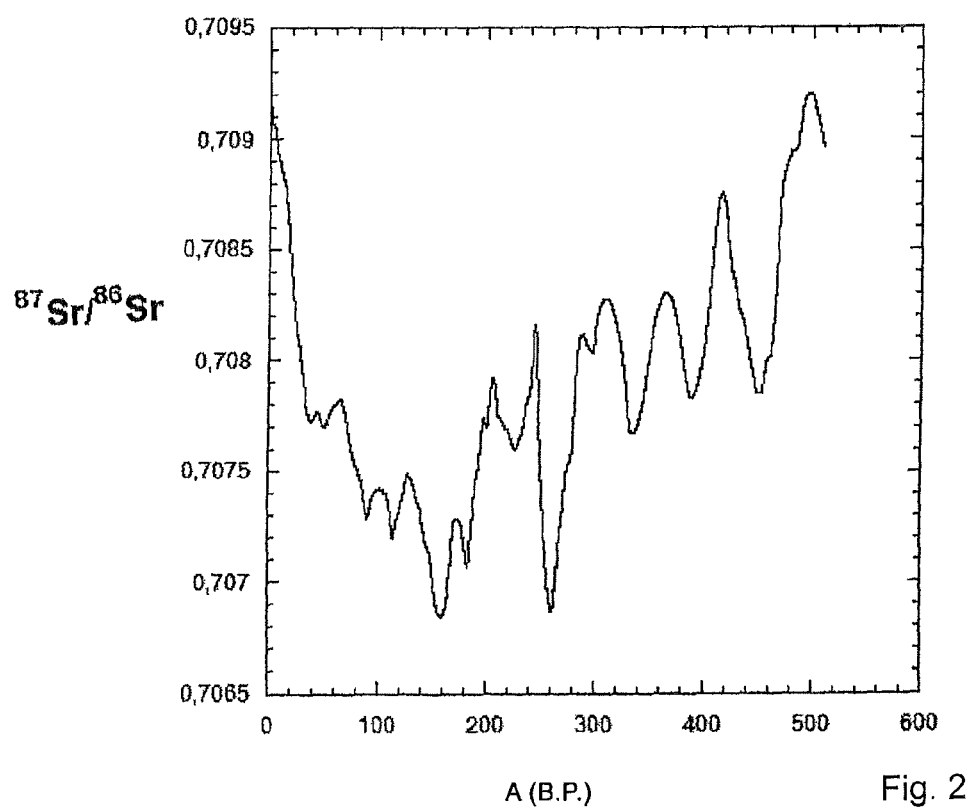
FIG. 2 shows a $^{87}$Sr/$^{86}$Sr curve of Phanerozoic seawater. By determining the $^{87}$Sr/$^{86}$Sr value of calcite (CC) the age of the parent solution (BS) can be determined.
Figure 3:
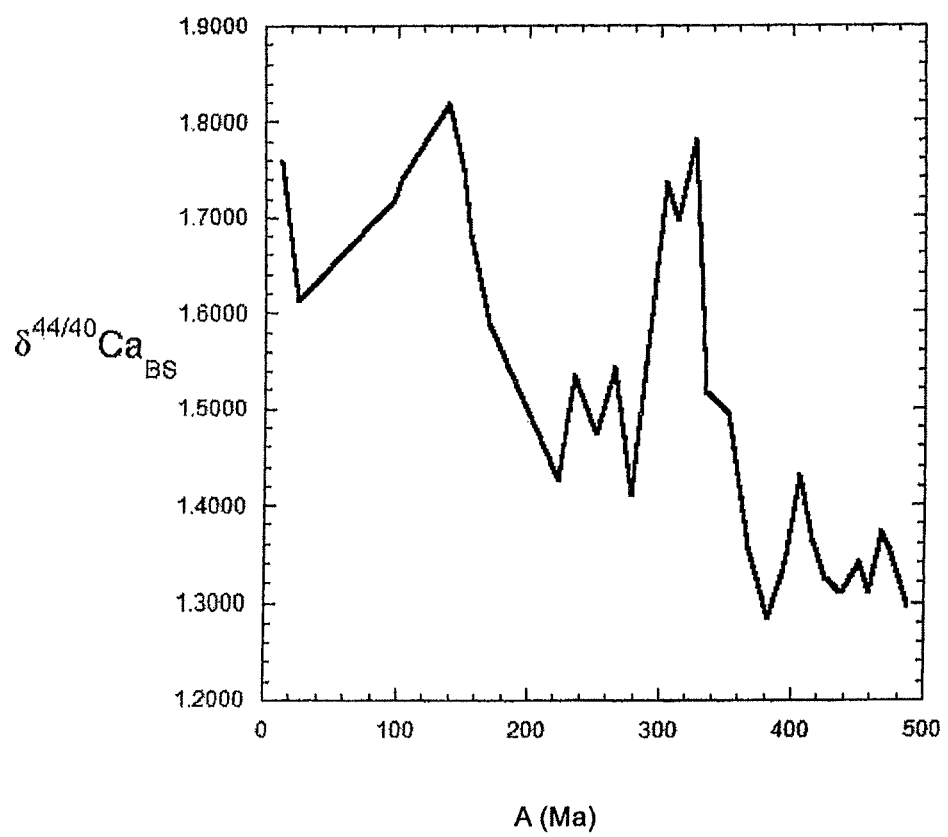
FIG. 3 shows the $\delta^{44/40}$Ca$_{BS}$-curve for the Phanerozoic seawater, Using the age determined from the $^{87}$Sr/$^{86}$Sr-curve, now the $\delta^{44/40}$Ca$_{BS}$-value necessary for computation van be determined.

In FIG. 1 it is assumed that at the earth surface (depth=0 m), a temperature of 15° C. prevails. The corresponding isotope value reflects the value of the $\Delta^{44/40}$Ca$_{CC}$ which calcium carbonate precipitated from Jurassic sea water would assume at a temperature of 15° C.

The increase in $\Delta_{44/40}$Ca$_{CC}$ a values adopted here reflects the geogenic temperature with an increase of 0.033° C./m. A $\Delta^{44/40}$Ca$_{CC}$=0 is assumed at a temperature of 73° C. and an associated depth of 1750 m. Information beyond are no longer possible because the $\Delta^{44/40}$Ca$_{cc}$-value cannot be positive.

The invention will now be illustrated by the following examples with the understanding that the universality of this teaching is not limited thereby.

A calcium carbonate sample taken at 700 m depth yielded, for example, the following results:

Sampling: Sampling is carried out on the drilled rock, usually a piece of drill core. We are looking for core segments where the porosity is reduced by incorporating recognizable white calcium carbonate. From this material, using a hammer, or better yet a cutter or hollow drill, a better piece of the rock, about 5 cm$^3$, is separated from the drill core. This hand rock sample is documented. A part of the h hand rock sample is pulverized, and an X-ray diffraction is carried out to determine the percentage of calcium carbonate as well as the polymorphism, and also, whether the calcium carbonate is present as calcite or aragonite. After this work, the calcium carbonate is dissolved out with a weak acid, for example, formic acid or 2 N HNO$_3$. The acid will be weak, so that no calcium is extracted from the non-calcium carbonate host rock, i.e., it is made sure that the original calcium isotopic composition of the precipitated calcium carbonate in the rock can be measured.

Measurement: The $^{44}$Ca/$^{40}$Ca-isotope ratio is determined by mass spectrometry using either the thermal ionization- or plasma-mass spectrometry. In the case of thermal ionization mass spectrometry, a Ca spike of known isotopic composition must be introduced into the solution before the measurement, in order after measuring to calculate out the mass discrimination during thermal ionization mass spectrometry.

In the plasma-mass spectrometry likewise a spike can also be added to in order to increase the precision of the measurement. The measurement can also be performed using the plasma mass spectrometer by means of the so-called "bracketing standard method", in which the correction for the mass discrimination in the plasma mass spectrometer is carried out by normalization to a standard known isotopic composition. The peculiar feature of plasma mass spectrometry of calcium is that you cannot measure the $^{44}Ca/^{40}Ca$ ratio directly as a rule, as there is an isobar effect with $^{40}Ar$, which functions as a carrier gas in the unit. In order to arrive at values therefore first the $^{42}Ca/^{44}Ca$-relationship is measured and then converted to the $^{44}Ca/^{40}Ca$ ratio.

In general, the method provides a slightly better thermionic precision than the plasma process, however, sample throughput in the plasma process is higher.

In Table 1 an example of an (EXCEL)-based data analysis for the calculation of precipitation temperatures using the Ca-isotope values ($\delta^{44/40}Ca$) can be seen.

TABLE 1

| 1 Sample | 2 $\delta^{44/40}Ca$ (o/oo) | 3 stat. error (o/oo) | 4 $\delta^{44/40}Ca$ (o/oo) | 5 T $\delta_{44/40Ca}$ (° C.) | 6 stat. error (° C.) |
|---|---|---|---|---|---|
| 1 | 0.63 | 0.12 | −0.52 | 47 | 9 |
| 2 | 0.97 | 0.27 | −0.18 | 64 | 18 |
| 3 | 0.85 | 0.08 | −0.3 | 58 | 5 |
| 4 | 0.84 | 0.09 | −0.31 | 58 | 6 |
| 5 | 0.7 | 0.21 | −0.45 | 51 | 15 |
| 6 | 1.06 | 0.16 | −0.09 | 69 | 10 |
| 7 | 1.32 | 0.19 | 0.17 | 82 | 12 |
| 8 | 0.88 | 0.17 | −0.27 | 60 | 11 |
| 9 | 0.67 | 0.33 | −0.48 | 49 | 24 |
| 10 | 1.14 | 0.16 | −0.01 | 73 | 10 |
| 11 | 1.75 | 0.07 | 0.6 | 103 | 4 |
| 12 | 1.31 | 0.22 | 0.16 | 81 | 14 |
| 13 | 1.13 | 0.08 | −0.02 | 72 | 5 |

Seawater value: 1.15

Column 1 contains the sample number. Column 2 contains the measured Ca isotope value ($\delta^{44/40}Ca$) and column 3 the associated statistical measurement error. In column 4 there is $\delta^{44/40}Ca$, which results from the subtraction of the values in column 3 and the seawater value, which is determined from the age of the solution. the age of the solution, usually seawater, is determined from their $^{87}Sr/^{86}Sr$-Isotopic yields. In column 5, the precipitation temperature in ° C. is then calculated (T $\delta^{44/40Ca}$(° C.)) from the values of column 4 and Equation 1. The statistical error for the temperature in column 6 is determined from the values in columns 3, 4 and 5.

$$T(° C.) = (\Delta^{44/40}Ca + 1.46)/0.02 \quad (1)$$

In FIG. 4, the calculated temperature values (in ° C.) of Table 1 are now shown as a function of their depth. The symbols represent very specific drill sites. The arrows in the figure indicate the average precipitation temperatures for the various symbols or locations. Together with the data points of different locations, the thermal gradient (equation 2) is also shown.

$$T_{geogenic} = 15° C. + (0.033° C./m) * Depth(m) \quad (2)$$

FIG. 4 shows that the precipitation temperatures (° C.), as determined using the measured Ca isotope ratios, do not coincide with the values of the geogenic temperature gradient (broken line) and indicate too great a depth relative to the temperature. The latter is due to the fact that the carbonates precipitated at an earlier date which corresponds to the depth, but were later displaced by a more accelerated subsiding to a greater depth.

From FIG. 4 it can be seen that the precipitation temperatures (T $\delta_{44/40Ca}$) assume a higher depth at the same temperature. Thereby a large number of measurements at a depth of about 2500 m show a temperature of ~50° C. The geogenic temperature gradient already shows between ~1500 m a temperature of ~50° C. In contrast, a temperature of ~90° C. would be expected at ~2500 m.

This apparent discrepancy is based thereon, that the carbonates have been precipitated at an earlier time, namely, when the rock, corresponding to the geologic deposit, was at a depth of ~1500 m. Since the precipitation of carbonates is always associated with the maturation of petroleum, this depth, or rather the associated age, marks the beginning of the oil migration into the reservoir rock.

The age and subsidence history can be calculated from the $^{87}Sr/^{86}Sr$-relationship. Here, in the specific case, the measured $^{87}Sr/^{86}Sr$-relationship of the host rock is ~0.7075 which corresponds to a geologic age of ~190 Ma. From the known present-day drilling depth of ~2500 m, an average subsidence rate of ~13 m/Ma (2500 m/190 Ma) can be calculated. From the precipitation depth of ~1500 m, there results a time of precipitation of ~115 Ma. These relationships can now be shown in an empirical age-depth relationship (empirically developed basin mod& FIG. 5).

This basin model determined empirically using the measured Ca and Sr isotopic ratios can be now compared with the basin model based on theoretical assumptions and seismic profiles. Ideally the results match, in the case of discrepancy a calibration of the theoretical model can be carried out on the basis of the empirical model of the basin.

LIST OF REFERENCE NUMERALS

A age
D depth, drilling depth
G geothermal gradient
T temperature
xx rock position (0.033° C./m)
x1 rock position on the surface
x2 rock position at approximate timing and depth of the CaCO3 precipitation
x3 rock position today

The invention claimed is:

1. A method for validating or calibrating a sedimentary basin model by determining an age depth relationship, the method comprising:
  obtaining a mathematical model of a sedimentary basin plotting the age-depth relationship of rocks to be validated or calibrated,
  i. obtaining a porous sample of sedimentary rock from a predetermined depth, the sedimentary rock including calcite,
  ii. determining the geologic age of the sedimentary rock,
  iii. dissolving calcite from the sample of the sedimentary rock using a dilute acid,
  iv. determining a Ca isotope ratio of two different Ca isotopes,
  v. determining the age of a solution in the sedimentary rock by determining a Sr-isotope ratio of $^{87}Sr/^{86}Sr$ and referencing this ratio with available data regarding the relationship between age and ratio of $^{87}Sr/^{86}Sr$, vi. determining the Ca isotopic ratio of a Bulk Solution by referencing the age of v. with known correlations or measuring the Ca isotopic ratio using Phanerozoic seawater from the pores of the sample of the sedimentary rock, vii. calculating the difference between the Ca isotope ratio step iv and step vi, viii. determining the CaCO$_3$-precipitation temperature (Tprecipitation) using the difference calculated in step vii by referencing with available data [p. 3/4], ix. determining CaCO$_3$ precipitation depth for the determination of the fixed point in its depth position X(m) in which the CaCO$_3$ has precipitated from a parent solution at known geothermic gradient, and x. using the product of step ix to validate or calibrate the basin model.

2. The method according to claim 1, wherein the ratio of Ca isotopes $^{40}$Ca and $^{44}$Ca ($^{44}$Ca/$^{40}$Ca) is used for determining an isotopic ratio of the precipitated CaCO$_3$ (CC).

3. A method according to claim 1, wherein a calculation of an Ca-isotopic difference ($\Delta^{44/40}$Ca) between a geological known solution (BS) and that CaCO$_3$ (CC), precipitated from the solution, is based on $$(\Delta^{44/40}Ca = \delta^{44/40}Ca_{CC} - \delta^{44/40}Ca_{BS})$$

at a known $\delta^{44/40}$ Ca$_{BS}$.

4. The method according to claim 1, wherein in the case of an unknown $\delta^{44/40}$ Ca$_{BS}$ a separation of the strontium ions (Sr$^{2+}$) in the solution, recovered from the precipitated calcium carbonate by dissolving out of sedimentary rocks by dilute acids, is carried out via ion chromatography, a Sr-isotope ratio $^{87}$Sr/$^{86}$Sr is determined for the two Sr-isotopes $^{87}$Sr and $^{86}$Sr, and a determination of the Ca isotopic difference is carried out by comparing the determined Sr-isotope ratio with a known Sr-isotope ratio of Phanerozoic seawater.

5. The method according to claim 1, wherein the determination of the CaCO$_3$-precipitation temperature is based on the relationship $\Delta^{44/40}$Ca(‰)=0:02 (‰/° C.)*Temperature(° C.)−1.46‰ according to the following equation 1:

$$T(°C.) = \frac{\Delta^{44/40}Ca + 1.46}{0.02}. \qquad \text{Equation 1}$$

6. The method according to claim 1, wherein the determination of the CaCO$_3$ precipitation depth (X(m)) occurs according to the following Equation 2:

$$X(m) = \frac{\delta^{44/40}Ca_{CC} - \delta^{44/40}Ca_{BS} + 1.16}{0.00066}. \qquad \text{Equation 2}$$

7. The method according to claim 1, wherein the actual temperature gradient or distribution is detected by a direct temperature measurements in the borehole from which the sample is taken.

* * * * *